(12) United States Patent
Park et al.

(10) Patent No.: US 11,540,738 B2
(45) Date of Patent: Jan. 3, 2023

(54) PPG SENSOR AND METHOD OF OPERATING THE SAME

(71) Applicant: SAMSUNG ELECTRONICS CO., LTD., Suwon-si (KR)

(72) Inventors: Jeong Ho Park, Seoul (KR); Long Yan, Hwaseong-si (KR); Eric Hyun Surk Ryu, Hwaseong-si (KR); Seoung Jae Yoo, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 415 days.

(21) Appl. No.: 16/749,149

(22) Filed: Jan. 22, 2020

(65) Prior Publication Data

US 2020/0390344 A1 Dec. 17, 2020

(30) Foreign Application Priority Data

Jun. 17, 2019 (KR) .................. 10-2019-0071376

(51) Int. Cl.
| | |
|---|---|
| G06K 9/00 | (2022.01) |
| A61B 5/026 | (2006.01) |
| H04N 5/378 | (2011.01) |
| H04N 5/374 | (2011.01) |
| G06T 7/136 | (2017.01) |
| A61B 5/0295 | (2006.01) |
| G06T 7/00 | (2017.01) |

(52) U.S. Cl.
CPC .......... *A61B 5/0261* (2013.01); *A61B 5/0295* (2013.01); *G06T 7/0012* (2013.01); *G06T 7/136* (2017.01); *H04N 5/378* (2013.01); *H04N 5/3741* (2013.01); *G06T 2207/30076* (2013.01)

(58) Field of Classification Search
CPC ... A61B 5/0261; A61B 5/0295; A61B 5/0037; A61B 5/02416; A61B 2562/0233; A61B 5/7221; A61B 2560/0209; A61B 5/0059; A61B 5/02444; A61B 5/7225; G06T 7/0012; G06T 7/136; G06T 2207/30076; H04N 5/3741; H04N 5/378; H04N 5/3454; H04N 5/3698; H04N 5/345
See application file for complete search history.

(56) References Cited

U.S. PATENT DOCUMENTS

| | | | |
|---|---|---|---|
| 8,666,116 B2 * | 3/2014 | Kirenko | G06T 5/50 |
| | | | 382/128 |
| 9,005,129 B2 | 4/2015 | Venkatraman et al. | |
| 9,307,917 B2 | 4/2016 | Hong et al. | |

(Continued)

FOREIGN PATENT DOCUMENTS

| | | |
|---|---|---|
| KR | 10-880392 B1 | 1/2009 |
| KR | 10-2016-0028093 A | 3/2016 |
| WO | WO 2019/016191 A1 | 1/2019 |

*Primary Examiner* — Shervin K Nakhjavan
(74) *Attorney, Agent, or Firm* — Lee IP Law, P.C.

(57) ABSTRACT

A photoplethysmogram (PPG) sensor includes a pixel array that collects light, a pixel sampler that converts the light collected through the pixel array into a plurality of pixel data, an effective area determiner that determines an effective area and a non-effective area of the pixel array based on the pixel data, a power controller that is operable to cut off power to the non-effective area of the pixel array, and a PPG data generator that generates PPG data from pixel data corresponding to the effective area among the pixel data.

20 Claims, 9 Drawing Sheets

(56) References Cited

U.S. PATENT DOCUMENTS

| | | | |
|---|---|---|---|
| 9,311,825 B2 | 4/2016 | Lusted et al. | |
| 9,538,106 B2* | 1/2017 | McMahon | H04N 5/3577 |
| 9,686,485 B2* | 6/2017 | Agranov | H04N 5/369 |
| 10,779,773 B2* | 9/2020 | Freeman | A61B 5/14551 |
| 2012/0162081 A1* | 6/2012 | Stark | G06F 3/0202 |
| | | | 345/168 |
| 2014/0243622 A1 | 8/2014 | Crowe et al. | |
| 2015/0335274 A1* | 11/2015 | Chang | A61B 5/6826 |
| | | | 600/479 |
| 2016/0022157 A1 | 1/2016 | Melker et al. | |
| 2016/0220130 A1 | 8/2016 | Han et al. | |
| 2017/0041564 A1* | 2/2017 | Konstantatos | H01L 27/14614 |
| 2017/0337413 A1* | 11/2017 | Bhat | A61B 5/0075 |
| 2018/0217665 A1* | 8/2018 | Konstantatos | G06F 3/011 |
| 2018/0373380 A1* | 12/2018 | Wang | A61B 5/0077 |

* cited by examiner

PPG SENSOR AND METHOD OF OPERATING THE SAME

Korean Patent Application No. 10-2019-0071376, filed on Jun. 17, 2019, in the Korean Intellectual Property Office, and entitled: "PPG Sensor and Method of Operating the Same," is incorporated by reference herein in its entirety.

BACKGROUND

1. Field

Embodiments relate to a photoplethysmogram (PPG) sensor and a method of operating the same.

2. Description of the Related Art

A photoplethysmogram (PPG) sensor obtains a PPG signal from light reflected from blood flow using a CMOS image sensor (CIS). PPG sensors are often mounted on wearable devices such as smart watches or small devices such as wireless earphones.

SUMMARY

Embodiments are directed to a photoplethysmogram (PPG) sensor, including a pixel array that collects light, a pixel sampler that converts the light collected through the pixel array into a plurality of pixel data, an effective area determiner that determines an effective area and a non-effective area of the pixel array based on the pixel data, a power controller that is operable to cut off power to the non-effective area of the pixel array, and a PPG data generator that generates PPG data from pixel data corresponding to the effective area among the pixel data.

Embodiments are also directed to a photoplethysmogram (PPG) sensor, including a pixel array that collects light, a pixel sampler that converts the light collected through the pixel array into a plurality of pixel data, a light amount determiner that determines whether to cut off power based on amounts of the collected light for the pixel data, a power controller that is operable to cut off power to the pixel array according to a command from the light amount determiner, and a PPG data generator that generates PPG data from the pixel data.

Embodiments are also directed to a method of operating a photoplethysmogram (PPG) sensor, the method including converting light collected through a pixel array into a plurality of pixel data, determining an effective area and a non-effective area of the pixel array based on the pixel data, cutting off power to the non-effective area of the pixel array, and generating PPG data from pixel data corresponding to the effective area among the pixel data.

Embodiments are also directed to a photoplethysmogram (PPG) system, including a light source, a PPG sensor arranged to receive light, emitted by the light source, that is reflected from skin of a user, and an application receiving PPG data from the PPG sensor. The PPG sensor may include a pixel array that collects the light reflected from the skin of the user, a pixel sampler that converts the light collected through the pixel array into a plurality of pixel data, an effective area determiner that determines an effective area and a non-effective area of the pixel array based on the pixel data, a power controller that is operable to cut off power to the non-effective area of the pixel array, and a PPG data generator that generates the PPG data from pixel data corresponding to the effective area among the pixel data.

BRIEF DESCRIPTION OF THE DRAWINGS

Features will become apparent to those of skill in the art by describing in detail example embodiments with reference to the attached drawings in which.

DETAILED DESCRIPTION

Figure 1:
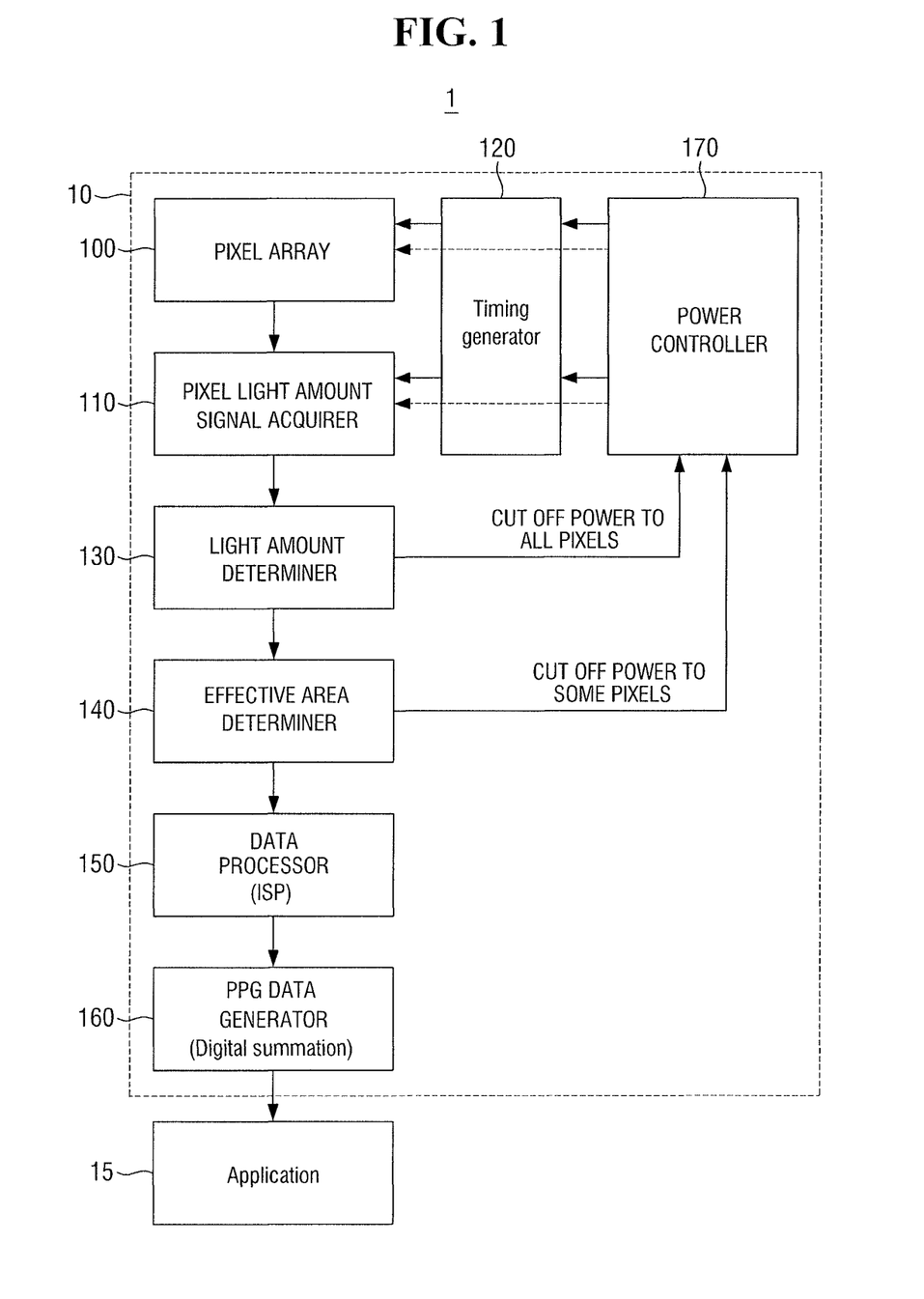
FIG. 1 illustrates a photoplethysmogram (PPG) sensing device according to an example embodiment.

FIG. 1 illustrates a photoplethysmogram (PPG) sensing device according to an example embodiment.

Referring to FIG. 1, a PPG sensing device 1 according to an example embodiment may include a PPG sensor 10 and an application 15.

The PPG sensing device 1 may measure blood flow changes by irradiating light to the skin at a short distance. The PPG sensing device 1 may be mounted on a wearable device such as a smart watch or a fitness band or a small device such as a wireless earphone and may be used to measure, e.g., a heart rate. When the PPG sensor 10 generates PPG data by measuring blood flow changes, the application 15 may implement various functions by utilizing the PPG data.

The PPG sensor 10 may include a pixel array 100, a pixel light amount signal acquirer 110, a timing generator 120, a light amount determiner 130, an effective area determiner 140, a data processor 150, a PPG data generator 160, and a power controller 170. The pixel array 100 may collect light through an optical system such as a lens.

In an example embodiment, the pixel array 100 may be implemented as a photodiode array. The pixel array 100 may be an active pixel sensor (APS) array and may include pixels having various structures. For example, the pixel array 100 may be implemented as a three transistor active pixel sensor (3-Tr APS) in which one pixel includes three transistors and one photodiode or a 4-Tr APS in which one pixel includes four transistors and one photodiode.

The pixel array may have a plurality of rows and a plurality of columns. The pixel light amount signal acquirer 110 may select or not select, e.g., deselect, a specific row among the rows constituting the pixel array 100 by enabling or disabling the specific row.

The pixel light amount signal acquirer 110 may sample light collected through the pixel array 100 and provide corresponding pixel data. The pixel light amount signal acquirer 110 may include one or more of a correlated double sampler (CDS) that may be used to remove noise generated when pixels are read out, an analog-digital converter (ADC) that may be used to convert analog pixel signals into digital data, and a trans-impedance amplifier (TIA) that may be used to convert photocurrents generated by photodiodes into electrical signals.

In another example embodiment, the pixel array 100 may be implemented as a digital pixel sensor array having an array of digital pixel sensors that perform analog-digital conversion. The digital pixel sensor array may include one or more of an ADC and a digital memory in each pixel, and may immediately convert an electrical signal generated from light collected through the optical system into a digital signal and store the digital signal in the digital memory. Accordingly, the digital pixel sensor may output a digital signal instead of a voltage signal.

When the pixel array 100 is implemented as a digital pixel sensor array, the internal configuration of the pixel light amount signal acquirer 110 may be different from when the pixel array 100 is implemented as an APS array. Like the APS array, the pixel light amount signal acquirer 110 may select or not select, e.g., deselect, a specific row by enabling or disabling the specific row among the rows constituting the pixel array 100.

The timing generator 120 may select or not select, e.g., deselect, a specific column among the columns constituting the pixel array 100 by enabling or disabling the specific column. The timing generator 120 may be operated and used together with the pixel light amount signal acquirer 110 to select or not select, e.g., deselect, a specific pixel in the pixel array 100. Thus, the pixel light amount signal acquirer 110 and the timing generator 120 may select or not select, e.g., deselect, a specific pixel among a plurality of pixels constituting the pixel array 100 by enabling or disabling a row and a column in which the specific pixel is located.

The power controller 170 may supply power to the pixel array 100 or cut off power to the pixel array 100. For example, the power controller 170 may cut off power to the whole of the pixel array 100 or part of the pixel array 100 by operating together with the light amount determiner 130 or the effective area determiner 140, as described in further detail below.

When the power controller 170 cuts off power to part of the pixel array 100, it may cut off power to pixels corresponding to a specific row by controlling the pixel light amount signal acquirer 110, may cut off power to pixels corresponding to a specific column by controlling the timing generator 120, or may cut off power only to a specific pixel by using both the pixel light amount signal acquirer 110 and the timing generator 120.

The light amount determiner 130 may determine whether to cut off power to the pixel array 100 based on amounts of collected light for a plurality of pixel data. When the light amount determiner 130 determines that the power to the pixel array 100 is to be cut off, it may send a command to the power controller 170 to cut off power to all pixels of the pixel array 100. Then, the power controller 170 may cut off power to the pixel array 100 according to the command from the light amount determiner 130.

For example, when values of all or at least some of the pixel data exceed a predetermined first light amount reference value, the light amount determiner 130 may send a command to the power controller 170 to cut off power to the whole of the pixel array 100. Here, when the value of certain pixel data exceeds the predetermined first light amount reference value, it may indicate that the pixel data is not useful in the acquisition of PPG data because the light of the pixel data is saturated. Thus, the predetermined first light amount reference value may be set to a value statistically and/or empirically determined to determine whether the light of pixel data is saturated or not.

The light amount determiner 130 may send a command to the power controller 170 to cut off power to the whole of the pixel array 100 when the values of all of the pixel data exceed the first light amount reference value. In another implementation, the light amount determiner 130 may send a command to the power controller 170 to cut off power to the whole of the pixel array 100 when the values of some of the pixel data exceed the first light amount reference value. In the latter case, the light amount determiner 130 may send a command to the power controller 170 to cut off power to the whole of the pixel array 100 when the values of e.g., 80% of the pixel data exceed the first light amount reference value.

In another example, the light amount determiner 130 may send a command to the power controller 170 to cut off power to the whole of the pixel array 100 when the values of all or at least some of the pixel data are less than a predetermined second light amount reference value. Here, when the value of certain pixel data is less than the predetermined second light amount reference value, it may indicate that the pixel data is not useful in the acquisition of PPG data because the light of the pixel data is low. Thus, the predetermined second light amount reference value may be set to a value statistically and/or empirically determined to determine whether the light of pixel data is low or not.

The light amount determiner 130 may send a command to the power controller 170 to cut off power to the whole of the pixel array 100 when the values of all of the pixel data are less than the second light amount reference value. In another implementation, the light amount determiner 130 may send a command to the power controller 170 to cut off power to the whole of the pixel array 100 when the values of some of the pixel data are less than the second light amount reference value. In the latter case, the light amount determiner 130 may send a command to the power controller 170 to cut off power to the whole of the pixel array 100 when the values of, e.g., 75% of the pixel data are less than the second light amount reference value.

The effective area determiner 140 may distinguish between an effective area and a non-effective area of the pixel array 100 based on a plurality of pixel data. The effective area determiner 140 may send a command to the power controller 170 to cut off power to some pixels of the pixel array 100, e.g., pixels of a subset of the pixel array 100, that correspond to the non-effective area. Then, the power controller 170 may cut off power to the non-effective area of the pixel array 100 according to the command from the effective area determiner 140.

Details about how the effective area determiner 140 distinguishes between the effective area and the non-effective area of the pixel array 100 and the power controller 170 cuts off power to the non-effective area of the pixel array 100 will be described below with reference to FIGS. 2 through 6.

The data processor 150 may perform various image processing operations on a plurality of pixel data. For example, the data processor 150 may perform image signal processing (ISP) on pixel data corresponding to the effective area of the pixel array 100. Examples of the image signal processing may include general imaging processing operations such as interpolation, color correction, gamma correction, color space conversion, white balance adjustment, exposure adjustment, and special operations needed to process or adjust PPG data.

The PPG data generator 160 generates PPG data from a plurality of pixel data. For example, the PPG data generator 160 may generate PPG data from pixel data corresponding to the effective area of the pixel array 100, e.g., using digital summation.

In an example embodiment, the PPG data generator 160 may measure signal quality of the pixel data corresponding to the effective area of the pixel array 100 and continuously generate PPG data from the pixel data corresponding to the effective area when the measured signal quality is maintained at a predetermined quality reference value or higher. If the signal quality measured by the PPG data generator 160 is less than the predetermined quality reference value, the pixel light amount signal acquirer 110 may collect light again through the pixel array 100 and generate a plurality of new pixel data, and the effective area determiner 140 may distinguish between the effective area and the non-effective area of the pixel array 100 based on the new pixel data.

The application 15 may be implemented as hardware such as an electronic circuit, software such as an application program, or a combination of hardware and software that perform various functions using PPG data received from the PPG sensor 10.

In an example embodiment, the pixel light amount signal acquirer 110 may generate a plurality of pixel data by collecting light through the pixel array 100 according to a signal generated by a timer. For example, the pixel light amount signal acquirer 110 may generate a plurality of pixel data by collecting light through the pixel array 100 according to a signal generated when a user wears a wearable device or a wireless earphone, or according to a signal generated at predetermined intervals.

In an example embodiment, the pixel light amount signal acquirer 110 may generate a plurality of pixel data by collecting light through the pixel array 100 according to a signal generated by an external sensor. For example, when determining that a sensing value generated by an acceleration sensor or a proximity sensor is meaningful, the pixel light amount signal acquirer 110 may generate a plurality of pixel data by collecting light through the pixel array 100.

In an example embodiment, the pixel light amount signal acquirer 110 may generate a plurality of pixel data by collecting light through the pixel array 100 according to a user signal. For example, the pixel light amount signal acquirer 110 may generate a plurality of pixel data by collecting light through the pixel array 100 according to a signal generated by a user's manipulation.

Figure 2:
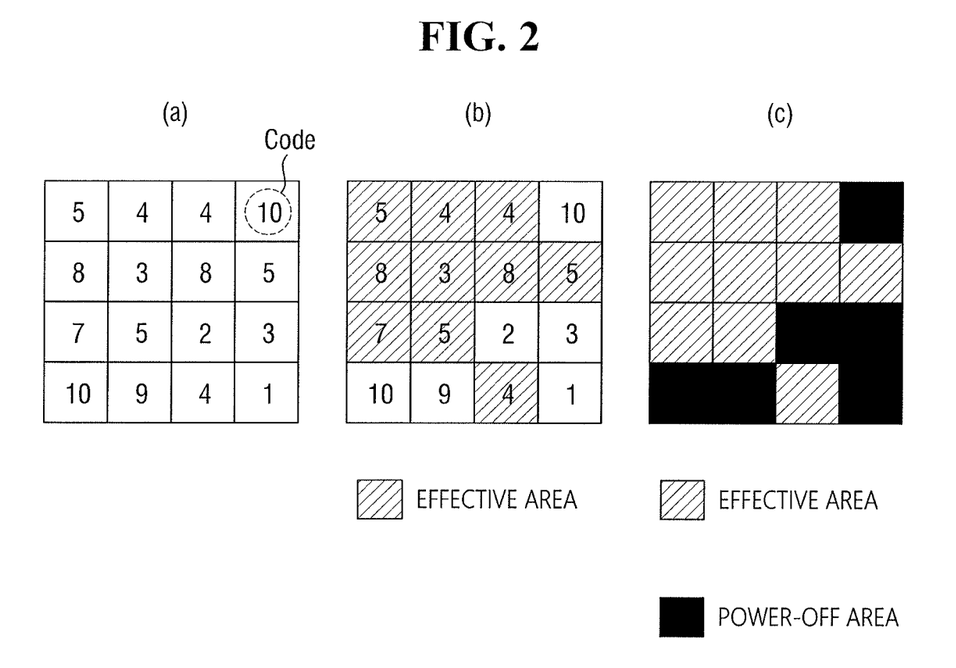
FIGS. 2 and 3 are diagrams for explaining an effective area determiner according to an example embodiment.
Figure 3:
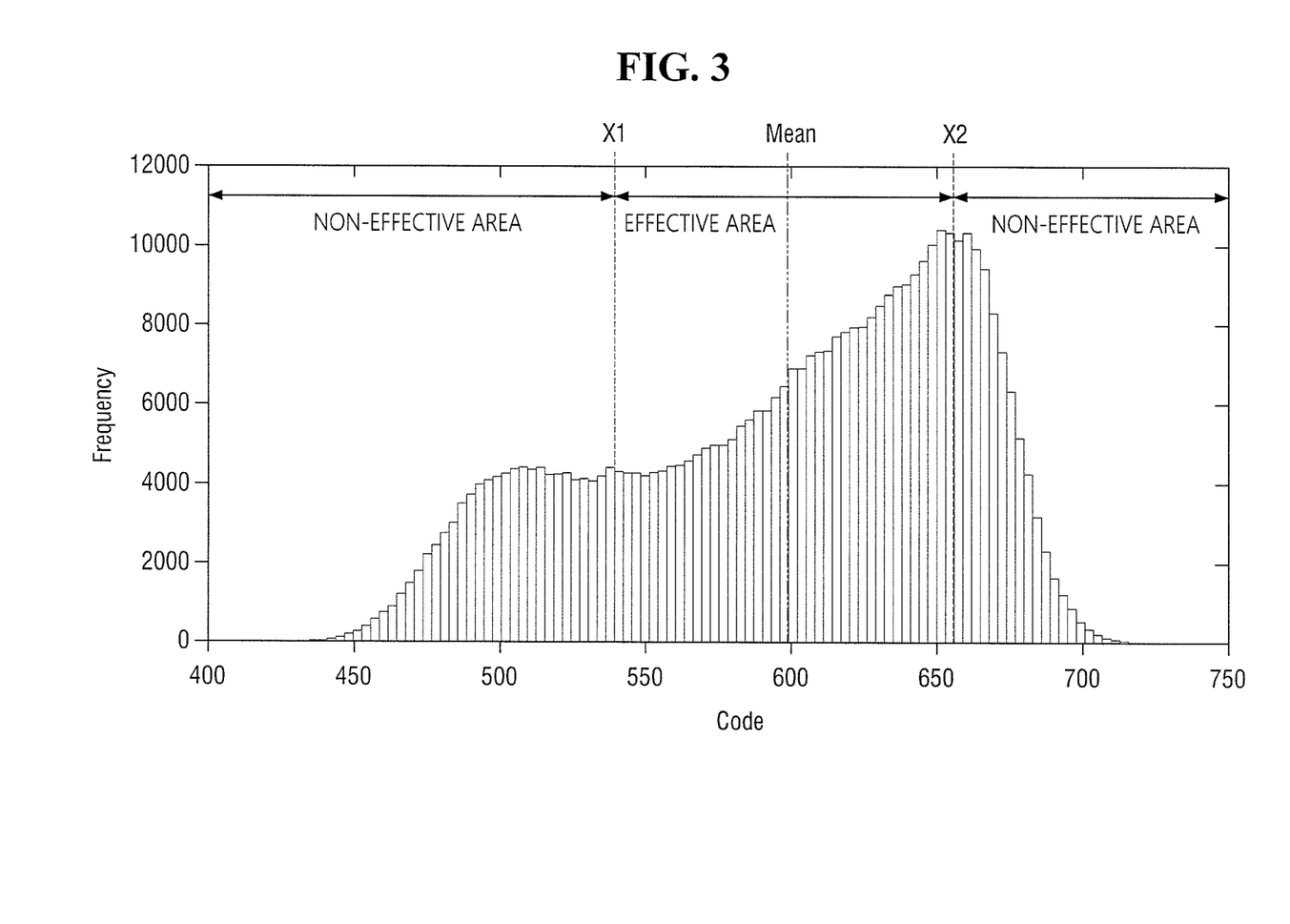

FIGS. 2 and 3 are diagrams for explaining the effective area determiner 140 according to an example embodiment.

In FIG. 2, (a) indicates pixels in part of the pixel array 100. For ease of description, pixel data in (a) is shown for light amounts that are represented by an integer of 1 to 10. The pixel data may be, e.g., output from the ADC of the pixel light amount signal acquirer 110 described above or may correspond to ADC code output from a digital pixel sensor array.

In FIG. 2, (b) shows an effective area that is indicated for pixels corresponding to pixel data values of 4 to 8 in (a). An example of setting the effective area and a non-effective area is described in detail below in connection with FIG. 3.

In (b) of FIG. 2, as an example, the pixels corresponding to the pixel data values of 4 to 8 may be determined to have meaningful values in the acquisition of PPG data. The other pixels (i.e., those that are not marked as the effective area, i.e., the non-effective area) may have pixel data values of 1, 2, 3, 9, or 10. The pixels corresponding to the pixel data values of 1, 2, 3, 9, and 10 may be determined to have light values that are not useful in the acquisition of the PPG data.

In FIG. 2, (c) shows the other pixels (i.e., those that are not marked as the effective area, i.e., the non-effective area) as being a power-off area. Since the pixels included in the power-off area, i.e., the non-effective area are not considered to provide useful values in the acquisition of PPG data, the power to these pixels may be cut off, thereby improving the power efficiency of the PPG sensor 10.

Although power is cut off on a pixel-by-pixel basis in FIG. 2 as an example, the power controller 170 may cut off power to pixels corresponding to a specific row and/or cut off power to pixels corresponding to a specific column according to a specific implementation purpose. For example, the power controller 170 may enable rows included in the effective area and disable rows included in the non-effective area by controlling the pixel light amount signal acquirer 110. When both effective and non-effective pixels are included in one row, whether the row will be determined to be effective or non-effective may be decided based on various criteria according to an operation policy of the PPG sensing device 1, the operation policy being determined according to a specific implementation purpose. As a simple example, a policy may be set in the PPG sensing device 1 such that a row is included in the effective area when the number of effective pixels in the row is greater than the number of non-effective pixels and is included in the non-effective area when the number of effective pixels in the row is smaller than the number of non-effective pixels.

As another example, the power controller 170 may enable columns included in the effective area of the pixel array 100 and disable columns included in the non-effective area by controlling the timing generator 120. When both effective and non-effective pixels are included in one column, whether the column will be determined to be effective or non-effective may be decided based on various criteria according to an operation policy of the PPG sensing device 1, the operation policy being determined according to a specific implementation purpose. As a simple example, a policy may be set in the PPG sensing device 1 such that a column is included in the effective area when 75% or more of pixels in the column are effective pixels and is included in the non-effective area when 75% or more of the pixels in the column are non-effective pixels.

Referring to FIG. 3, in order to set the effective area and the non-effective area in the pixel array 100, the effective area determiner 140 may set a first section reference value X1 and a second section reference value X2 based on a plurality of pixel data. The effective area determiner 140 may include pixel data, whose values exist between the first section reference value X1 and the second section reference value X2, in the effective area, and may include pixel data, whose values do not exist between the first section reference value X1 and the second section reference value X2, in the non-effective area. In the example shown in FIG. 3, the horizontal axis represents ADC code values that each pixel of the pixel array 100 can have, and the vertical axis represents the number of pixels (i.e., frequency) corresponding to each ADC code value in the pixel array 100.

In an example embodiment, the effective area determiner 140 may dynamically reset the first section reference value X1 and the second section reference value X2 during the operation of the PPG sensor 10. For example, if the mean is located too far to the right, the effective area determiner 140 may shift the second section reference value X2 to the left by multiplying the second section reference value X2 by a weight. As another example, the effective area determiner 140 may shift the first section reference value X1 or the second section reference value X2 to the left or right by multiplying at least one of the first section reference value X1 and the second section reference value X2 by a weight.

Figure 4:
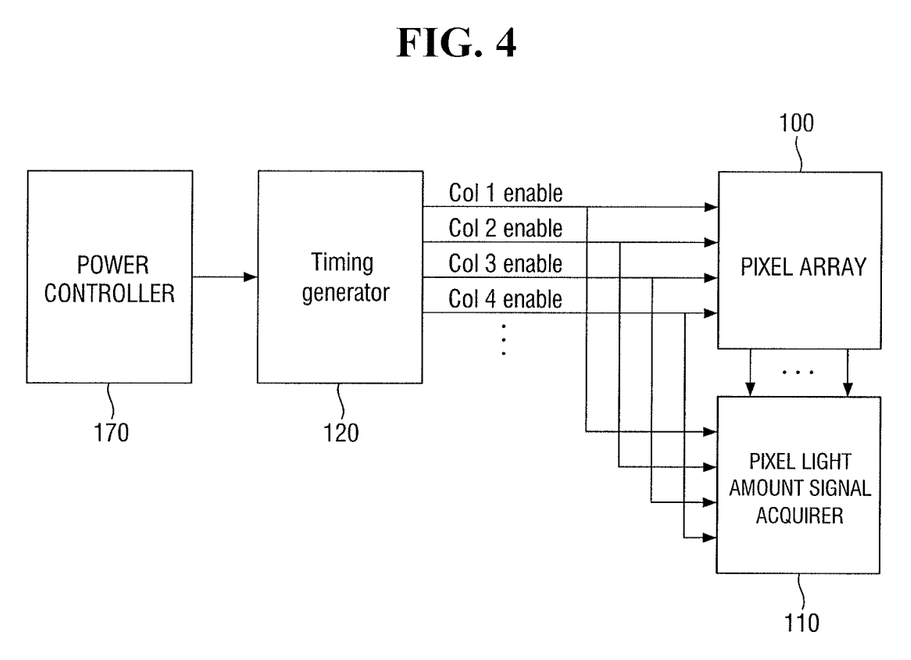
FIGS. 4 through 6 are diagrams for explaining a power controller according to an example embodiment.
Figure 5:
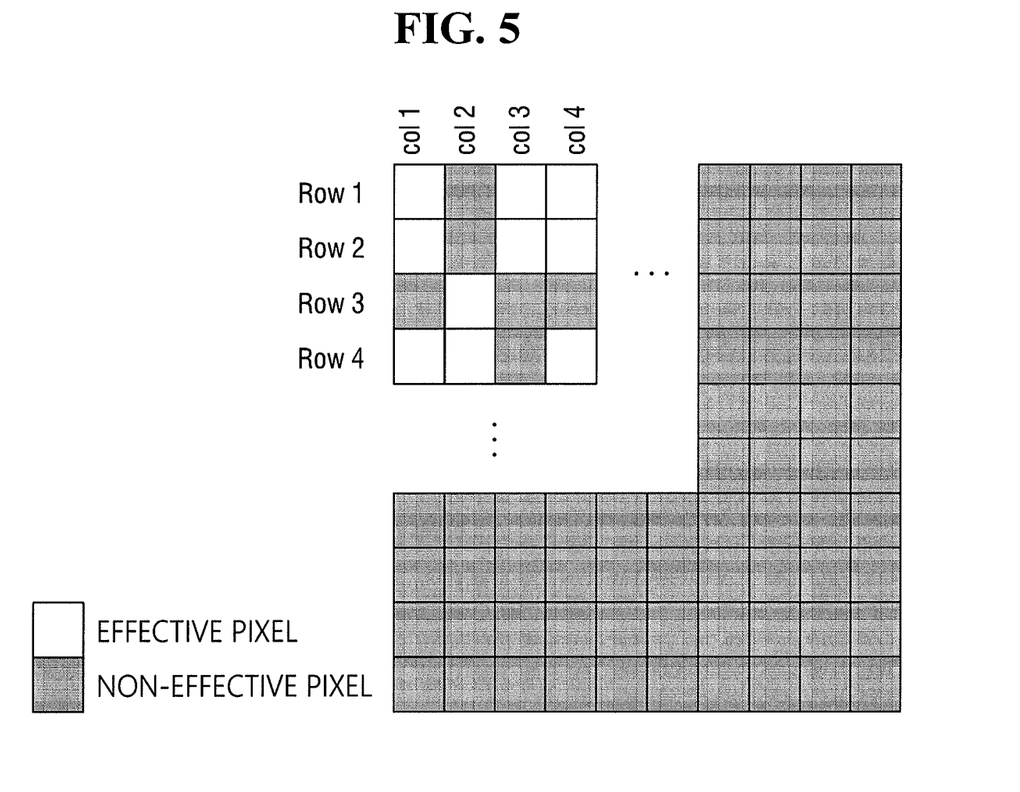
Figure 6:
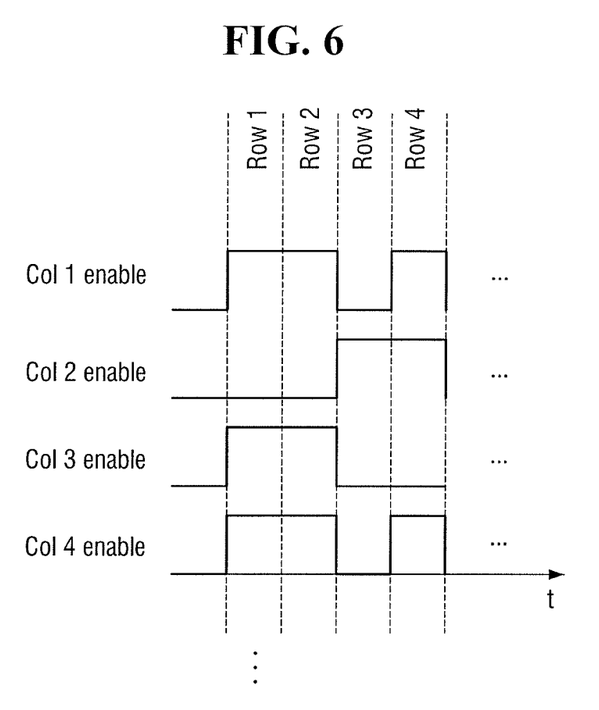

FIGS. 4 through 6 are diagrams for explaining a power controller according to an example embodiment.

Referring to FIGS. 4 through 6, a power controller 170 may enable rows and columns included in the effective area of the pixel array 100 and disable rows and columns included in the non-effective area of the pixel array 100 by controlling the pixel light amount signal acquirer 110 and the timing generator 120.

For example, FIG. 5 illustrates the pixel array 100 for an example case where the effective area of the pixel array 100 includes effective pixels corresponding to first, third, and fourth columns of a first row, pixels corresponding to first, third, and fourth columns of a second row, a pixel corresponding to a second column of a third row, and pixels corresponding to first, second, and fourth columns of a fourth row.

In this case, when the pixel light amount signal acquirer 110 selects the first row, the power controller 170 may set a column enable signal that is input to the first, third, and fourth columns to logic high, and the power controller 170 may set a column enable signal that is input to the second column to logic low by controlling the timing generator 120, thereby cutting off power to a pixel corresponding to the second column of the first row. Likewise, when the pixel light amount signal acquirer 110 selects the third row, the power controller 170 may set a column enable signal that is input to the second column to logic high, and the power controller 170 may set a column enable signal that is input to first, third, and fourth columns to logic low by controlling the timing generator 120, thereby cutting off power to pixels corresponding to the first, third, and fourth columns of the third row.

Figure 7:
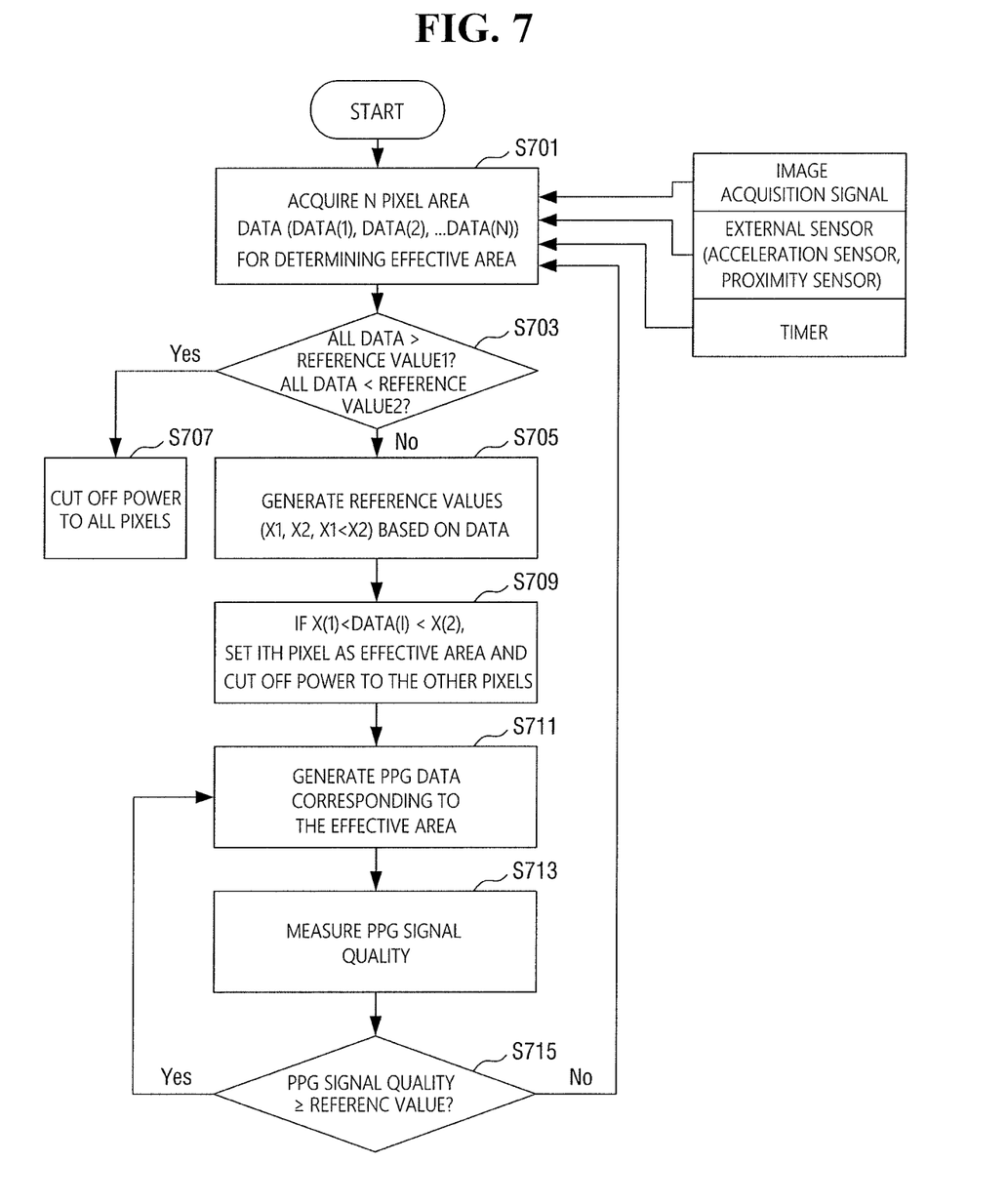
FIG. 7 illustrates a method of operating a PPG sensor according to an example embodiment.

FIG. 7 illustrates a method of operating a PPG sensor according to an example embodiment.

Referring to FIG. 7, a method of operating a PPG sensor 10 according to an example embodiment may include acquiring data for determining an effective area of a pixel array 100 (operation S701). The acquisition of the data (operation S701) may include converting light collected through the pixel array 100 into a plurality of pixel data.

In addition, the method may include determining whether to cut off power based on amounts of collected light for the pixel data (operation S703). In the determining of whether to cut off the power (operation S703), it may be determined whether values of all or at least some of the pixel data exceed a predetermined first light amount reference value. In the determining of whether to cut off the power (operation S703), it may be determined whether the values of all or at least some of the pixel data are less than a predetermined second light amount reference value.

If it is determined that the values of all or at least some of the pixel data exceed the predetermined first light amount reference value or are less than the predetermined second light amount reference value, the power to the pixel array 100 may be cut off based on the determination (operation S707).

If it is determined that the values of all or at least some of the pixel data do not exceed the predetermined first light amount reference value and are equal to or higher than the predetermined second light amount reference value, a first section reference value X1 and a second section reference value X2 may be set based on the pixel data (operation S705).

Of the pixel data, pixel data whose values exist between the first section reference value X1 and the second section reference value X2 may be included in the effective area, and pixels whose values do not exist between the first section reference value X1 and the second section reference value X2 may be included in an non-effective area, to thus distinguish between the effective area and the non-effective area of the pixel array 100 and to cut off power to the non-effective area (operation S709).

The cutting off of the power to the non-effective area (operation S709) may include enabling rows included in the effective area of the pixel array 100 and disabling rows included in the non-effective area, enabling columns included in the effective area of the pixel array 100 and disabling columns included in the non-effective area, or enabling rows and columns included in the effective area of the pixel array 100 and disabling rows and columns included in the non-effective area.

In an example embodiment, the first section reference value X1 and the second section reference value X2 may be dynamically reset during the operation of a PPG sensor 10.

Next, PPG data may be generated from pixel data corresponding to the effective area among the pixel data (operation S711).

Next, signal quality of the pixel data corresponding to the effective area may be measured (operation S713). When the signal quality is maintained at a predetermined quality reference value or higher, the PPG data may be continuously generated from the pixel data corresponding to the effective area (Yes in operation S715). On the other hand, when the signal quality is less than the predetermined quality reference value, a plurality of new pixel data may be generated (No in operation S715).

In an example embodiment, the generating of the pixel data may include generating a plurality of pixel data by collecting light through the pixel array 100 according to a signal generated by a timer.

In an example embodiment, the generating of the pixel data may include generating a plurality of pixel data by collecting light through the pixel array 100 according to a signal generated by an external sensor.

In an example embodiment, the generating of the pixel data may include generating a plurality of pixel data by collecting light through the pixel array 100 according to a user signal.

The method may further include performing image processing on the pixel data corresponding to the effective area.

Figure 8:
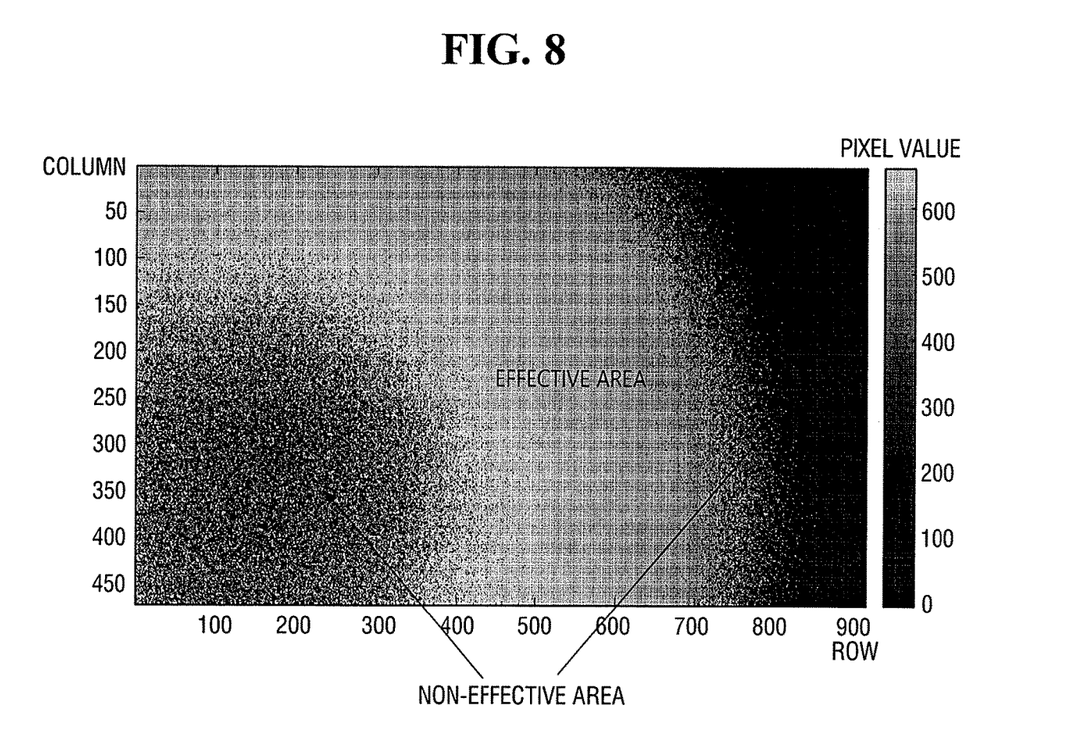
FIG. 8 is a diagram for explaining an example result of determining an effective area of a PPG sensor according to an example embodiment.

FIG. 8 is a diagram for explaining an example of determining the effective area of the PPG sensor 10 according to an example embodiment.

Referring to FIG. 8, about half of the pixels of the pixel array 100 are included in the effective area, and the other half are included in the non-effective area. Therefore, since the power controller 170 cuts off power to the non-effective area as described above, an apparent power reduction of the PPG sensor 10 is observed.

Figure 9:
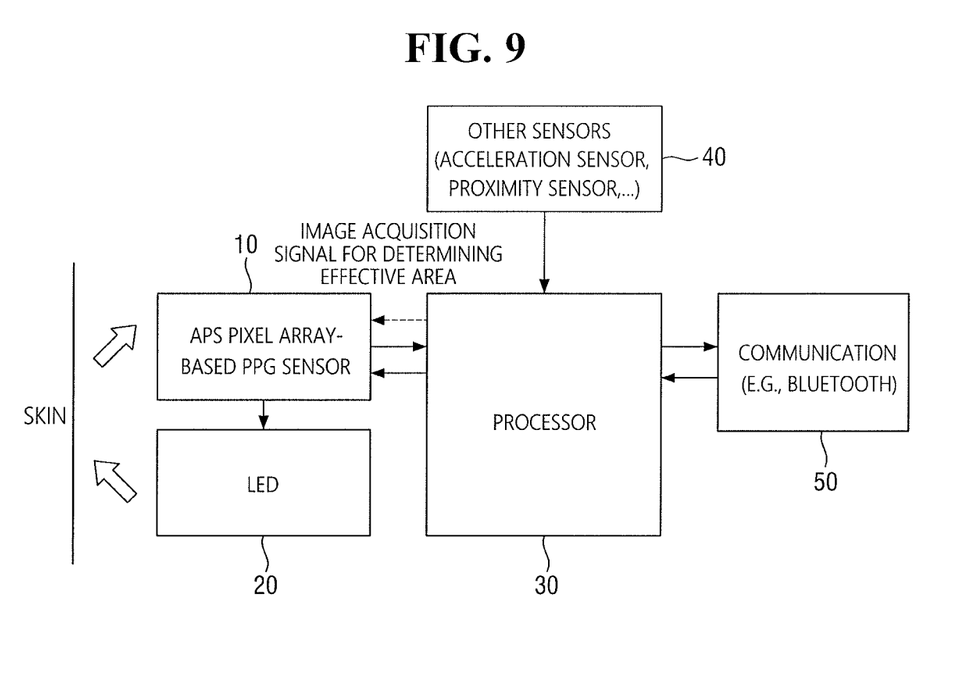
FIG. 9 is a diagram for explaining an example in which the PPG sensor according to an example embodiment is used.

FIG. 9 is a diagram for explaining an example in which a PPG sensor according to an example embodiment is used.

Referring to FIG. 9, a PPG sensor 10 according to an example embodiment may be used together with a light source 20. The light source 20 may be, e.g., a light emitting diode (LED) that illuminates the skin of a user. The PPG sensor 10 may be, e.g., an APS pixel array-based PPG sensor that collects light reflected from the skin, and may obtain PPG data from the collected light. The PPG sensor 10 may determine the effective area and the non-effective area of the pixel array 100 based on acquired image signals under the control of a processor 30 (e.g., an application processor (AP)) and may interconnect with an external sensor 40, e.g., an acceleration sensor or a proximity sensor as described above, and/or interconnect with other devices through a communication device 50, e.g., a Bluetooth module.

By way of summation and review, a PPG sensor may be set to operate for a long time in an environment in which very limited power is provided. As such, embodiments may minimize power consumption of the PPG sensor. Embodiments may provide a PPG sensor that improves power efficiency by reducing the power consumption of a pixel array and a method of operating the PPG sensor.

As those of skill in this art would appreciate, some aspects of the embodiments herein may be described and/or illustrated with reference to functional blocks, units, or modules. A block, unit, or module may be implemented by dedicated hardware, or as a combination of dedicated hardware to perform some functions and a processor (e.g., one or more programmed microprocessors and associated circuitry) to perform other functions. A block, unit, or module of the embodiments may be physically separated into two or more interacting and discrete blocks, units, or modules, or blocks, units, or modules may be physically combined into more complex blocks, units, or modules. Those skilled in the art will appreciate that these blocks, units, or modules can be physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units, or modules being implemented by microprocessors or similar, they may be programmed using software (e.g., microcode) to perform various functions discussed herein and may optionally be driven by firmware or software.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A photoplethysmogram (PPG) sensor, comprising:
a pixel array that collects light;
a pixel sampler that converts the light collected through the pixel array into a plurality of pixel data;
an effective area determiner that determines an effective area and a non-effective area of the pixel array based on the pixel data;
a power controller that is operable to cut off power to the non-effective area of the pixel array; and
a PPG data generator that generates PPG data from pixel data corresponding to the effective area among the pixel data, wherein:
the effective area determiner sets a first section reference value and a second section reference value based on the pixel data,
the effective area determiner includes pixel data, whose values exist between the first section reference value and the second section reference value among the pixel data, in the effective area, and
the effective area determiner includes pixel data, whose values do not exist between the first section reference value and the second section reference value among the pixel data, in the non-effective area.

2. The PPG sensor as claimed in claim 1, wherein the power controller enables rows included in the effective area and disables rows included in the non-effective area by controlling the pixel sampler.

3. The PPG sensor as claimed in claim 2, further comprising a timing generator that enables or disables columns of the pixel array, wherein the power controller enables columns included in the effective area and disables columns included in the non-effective area by controlling the timing generator.

4. The PPG sensor as claimed in claim 1, further comprising a light amount determiner that determines whether to cut off power based on amounts of light collected for the pixel data, wherein the power controller cuts off power to the pixel array according to a command from the light amount determiner.

5. The PPG sensor as claimed in claim 4, wherein the light amount determiner sends a command to the power controller to cut off power to the whole of the pixel array when values of all or at least some of the pixel data exceed a predetermined first light amount reference value.

6. The PPG sensor as claimed in claim 4, wherein the light amount determiner sends a command to the power controller to cut off power to the whole of the pixel array when values of all or at least some of the pixel data are less than a predetermined second light amount reference value.

7. The PPG sensor as claimed in claim 1, wherein the PPG data generator measures signal quality of the pixel data corresponding to the effective area and continuously generates the PPG data from the pixel data corresponding to the effective area when the signal quality is maintained at a predetermined quality reference value or higher.

8. The PPG sensor as claimed in claim 7, wherein the pixel sampler collects light again through the pixel array and generates a plurality of new pixel data when the signal quality measured by the PPG data generator is less than the quality reference value.

9. The PPG sensor as claimed in claim 1, wherein the pixel sampler generates the pixel data by collecting light through the pixel array according to a signal generated by a timer.

10. The PPG sensor as claimed in claim 1, wherein the pixel sampler generates the pixel data by collecting light through the pixel array according to a signal generated by an external sensor.

11. The PPG sensor as claimed in claim 1, wherein the pixel sampler generates the pixel data by collecting light through the pixel array according to a user signal.

12. A photoplethysmogram (PPG) sensor, comprising:
a pixel array that collects light;
a pixel sampler that converts the light collected through the pixel array into a plurality of pixel data;
a light amount determiner that determines whether to cut off power based on amounts of the light collected for the pixel data;
a power controller that is operable to cut off power to the pixel array according to a command from the light amount determiner; and
a PPG data generator that generates PPG data from the pixel data.

13. The PPG sensor as claimed in claim 12, wherein the light amount determiner sends a command to the power controller to cut off power to the whole of the pixel array when values of all or at least some of the pixel data exceed a predetermined first light amount reference value.

14. The PPG sensor as claimed in claim 12, wherein the light amount determiner sends a command to the power controller to cut off power to the whole of the pixel array when values of all or at least some of the pixel data are less than a predetermined second light amount reference value.

15. The PPG sensor as claimed in claim 12, further comprising an effective area determiner that determines an effective area and a non-effective area of the pixel array based on the pixel data, wherein the power controller cuts off power to the non-effective area of the pixel array.

16. The PPG sensor as claimed in claim 15, wherein:
the effective area determiner sets a first section reference value and a second section reference value based on the pixel data,
the effective area determiner includes pixel data, whose values exist between the first section reference value and the second section reference value among the pixel data, in the effective area, and
the effective area determiner includes pixel data, whose values do not exist between the first section reference value and the second section reference value among the pixel data, in the non-effective area.

17. The PPG sensor as claimed in claim 16, wherein the power controller enables rows included in the effective area and disables rows included in the non-effective area by controlling the pixel sampler.

18. The PPG sensor as claimed in claim 17, further comprising a timing generator that enables or disables columns of the pixel array, wherein the power controller enables columns included in the effective area and disables columns included in the non-effective area by controlling the timing generator.

19. A photoplethysmogram (PPG) system, comprising:
a light source;
the PPG sensor as claimed in claim 1, the PPG sensor being arranged to receive light, emitted by the light source, that is reflected from skin of a user; and
an application receiving PPG data from the PPG sensor.

20. A photoplethysmogram (PPG) system, comprising:
a light source arranged to emit light to skin of a user;
a pixel array including pixels, the pixel array being arranged to collect light that is reflected from the skin of the user; and
a power controller coupled to the pixel array, and configured to cut off power to a non-effective area of the pixel array while providing power to an effective area of the pixel array, wherein:
the effective area of the pixel array contains pixels of the pixel array that correspond to a light amount that is between a first reference value and a second reference value, and
the non-effective area of the pixel array contains pixels of the pixel array that correspond to a light amount that is not between the first reference value and the second reference value.

* * * * *